United States Patent [19]

Burns et al.

[11] 4,453,977

[45] Jun. 12, 1984

[54] LOW SILVER CONTAINING DENTAL AMALGAM ALLOYS

[75] Inventors: Charles F. Burns, Lansdowne; Edward J. Pilcicki, Gilbertsville, both of Pa.

[73] Assignee: Pennwalt Corporation, Philadelphia, Pa.

[21] Appl. No.: 364,135

[22] Filed: Jun. 15, 1982

[51] Int. Cl.$^3$ .................... B22F 1/00; C22C 5/06
[52] U.S. Cl. ........................ 75/255; 420/502; 420/504; 420/560; 420/527; 420/587; 420/589; 75/0.5 R
[58] Field of Search ............... 420/501, 502, 504, 506, 420/580, 587, 589; 75/251–255, 0.5 R

[56] References Cited

U.S. PATENT DOCUMENTS

| | | | |
|---|---|---|---|
| 3,954,457 | 5/1976 | Weikel | 420/502 |
| 3,963,484 | 6/1976 | Sarkar | 420/504 |
| 3,980,472 | 9/1976 | Asgar | 420/502 |
| 3,997,328 | 12/1976 | Aliotta et al. | 75/0.5 R |
| 3,997,329 | 12/1976 | Aliotta et al. | 75/0.5 R |
| 3,997,330 | 12/1976 | Aliotta et al. | 75/0.5 R |
| 4,015,981 | 4/1977 | Rogova et al. | 420/587 |
| 4,039,329 | 8/1977 | Youdelis | 75/255 |
| 4,164,419 | 8/1979 | Kaji et al. | 420/502 |
| 4,226,622 | 10/1980 | Aliotta et al. | 75/251 |
| 4,370,165 | 1/1983 | De Luca | 106/35 |

*Primary Examiner*—L. Dewayne Rutledge
*Assistant Examiner*—Christopher W. Brody

[57] ABSTRACT

Conventional or non-conventional dental amalgam alloys in the form of lathe-cut, spherical shaped or irregular shaped particles of silver, tin, copper and zinc are improved by adding to the alloys at least one compound selected from $Cu_6Sn_5$, $Cu_3Sn$ or a mixture thereof. The resulting dental alloy mixture is low in silver, is corrosion resistant, and is used as a filling for dental cavities after amalgamation with mercury.

3 Claims, No Drawings

LOW SILVER CONTAINING DENTAL AMALGAM ALLOYS

BACKGROUND OF THE INVENTION

The present invention relates to dental amalgam alloy mixtures and more particularly to low silver dental alloy mixtures of silver, tin, copper, and zinc which are improved by adding of $Cu_6Sn_5$, $Cu_3Sn$ or a mixture thereof.

Prior to the present invention, dental amalgam alloys generally contained from about 68 to about 72% by weight of silver, the remainder being composed of tin, copper, and zinc, although the inclusion of gold, indium, manganese, etc. is not uncommon. The high cost of silver warranted exploration of reduced silver content of dental amalgam alloys and the use of less expensive manufacturing techniques. Many patents have been granted on dental amalgam alloys trying to reduce the silver content. Copper was the element mostly used to reduce the silver content in the alloys. These new alloy systems focused on the addition of greater amounts of copper, in effect, to reduce and/or eliminate the weak, corrosive Gamma II phase ($Sn_7Hg$); in the amalgam, other elements and metallurgical techniques were incorporated such as, the blending of brazing alloys with conventional or non-conventional dental alloys, the adding of indium, manganese, gold, etc., and the producing of low silver (40%) and high silver (60%) single phase non-conventional spherical alloy compositions. Many of these systems include the lathe-cut and/or spherical or irregular shaped alloy particles with varying ranges of particle size distribution. Spherical and/or irregular shaped particles are produced by water and/or gas atomization, a technology that is well known in the art.

U.S. Pat. No. 4,015,981 (Rogova et al) disclosed an alloy consisting of gallium, tin and copper in the absence of silver. This alloy was prepared by mixing together a eutectic liquid gallium-tin alloy with a powdered copper, tin alloy of the formula $Cu_3Sn$. U.S. Pat. No. 4,234,339 (Aliotta et al) teaches a corrosion resistant dental alloy mixture of three alloys each containing silver, tin, and copper and being in the form of spherical particles, randomly shaped particles, and flake-like particles. U.S. Pat. No. 4,039,329 (Youdelis) teaches a mixture of 75% silver and about 25% tin as a base alloy in combination with indium up to 30%. This patent teaches that a portion of the base alloy can optionally be substituted with up to 6% copper and up to 2% zinc. None of the above patents teach the present invention.

STATEMENT OF THE INVENTION

In a dental amalgamable composition comprising about 50 to 95% by weight of at least one amalgamable alloy of
   40 to 75% by weight of silver,
   20 to 30% by weight of tin,
   2 to 30% by weight of copper, and
   0.5 to 30% by weight of at least one member selected from the group consisting of indium, zinc, gold, mercury, manganese, cadmium, and aluminum, the improvement comprising adding to this composition from about 5 to 50% by weight of at least one member selected from the group consisting of $Cu_6Sn_5$, $Cu_3Sn$, and a mixture thereof, wherein the member is in the form of lathe-cut, spherical shaped, or irregular shaped particles and has the composition of
   30 to 70% by weight of copper, and
   70 to 30% by weight of tin.

DETAILED DESCRIPTION OF THE INVENTION

The copper-tin compound of the present invention can be added to conventional or non-conventional amalgam alloys in the amount from about 5 weight percent to about 50 weight percent of the composition. The copper-tin compound and the conventional or non-conventional amalgam alloys can be in the form of lathe-cut particles, spherical shaped particles and irregular shaped particles or a combination of two or more of the particle shapes. A conventional type dental amalgam alloy generally contains a nominal composition of 70 weight percent of silver, 26 weight percent of tin, 3 weight percent of copper and 1 weight percent of zinc. Mechanically mixing or triturating equal weights of dental amalgam alloy and mercury causes the formation of metallic crystals as the amalgam solidifies; these formations consist of Gamma I and Gamma II compounds, a tin-mercury compound ($Sn_7Hg$), a silver-mercury compound ($Ag_2Hg_3$), $Cu_3Sn$, and $Cu_6Sn_5$, thus forming the matrices around the remaining unconsumed original Gamma particles ($Ag_3Sn$). The addition of the copper-tin compounds of the present invention to conventional or non-conventional amalgam alloys will initiate a metallurgical reaction by combining (blending) $Ag_3Sn$ and one or more copper-tin compounds of $Cu_6Sn_5$ and/or $Cu_3Sn$, will reduce Gamma II phase by dissociation of copper from the copper-tin phase, will reduce static creep, will increase general physical properties of the amalgam, and will drastically reduce the overall cost of the amalgam product by reducing the silver content in the amalgam.

Representative alloy compositions of the present invention are as follows:

(1) Dispersed phase alloys containing a blend of two or more alloys (typically consisting of a conventional phase alloy of silver, tin, copper and zinc and a dispersant phase alloy of silver-copper or silver-copper and other elements such as tin, indium, manganese, gold, cadmium, etc.) can have the addition of the copper-tin compound(s) to reduce the silver content of the blended alloy. The percentage of copper-tin can be adjusted from about 5 to 50 percent depending on the physical properties desired of the final amalgam.

(2) Non-conventional type dental amalgam alloys being spherical, irregular or, lathe-cut generally consist of silver, tin, and copper; they can also contain other elemental additives such as indium, manganese, gold, cadmium, etc., and have silver contents between 40 and 60 percent. The addition of from about 5 to about 50 percent of the copper-tin compounds reduces the total silver content in the alloy blend to from about 20 to 40 percent.

(3) Silver-copper eutectic, silver-copper eutectic plus tin, and similar compositions of from about 5 to about 50 percent may be diluted (blended) with copper-tin compounds to achieve low silver containing dental amalgam alloys. The preferred system is one that incorporates as much lathe-cut type alloy as possible for ease of production and low cost while producing a suitable dental amalgam alloy that will combine with mercury to yield physical properties as specified by the American Dental Association's Specification No. 1 (Dental Amalgam Alloys).

(4) This composition contains approximately 30-40% by weight of silver, 23-33% by weight of tin, 33-40% by weight of copper, and 0-2% by weight of zinc, after blending.

The blending alloys of this composition include the following compositions (all percents are by weight and the preferred amounts are in parenthesis):

Alloy component No. 1

Silver: 68-72% (70.5)
Tin: 24-28% (26.0)
Copper: 1-4% (2.5)
Zinc: 0-2% (1.0)

Alloy component No. 2

Silver: 70-74% (71.8)
Copper: 26-30% (28.2)

Alloy component No. 3

Tin: 55-65% (60.9)
Copper: 35-45% (39.1)

The most preferred blend is as follows:

Alloy component No. 1: 33.33%
Alloy component No. 2: 16.66%
Alloy component No. 3: 50.00%

An amalgam is made from such a blend by mixing with from about 40 to about 60 percent of mercury, yielding a plastic amalgam mass suitable for use as a dental restorative material; any or all of the alloy components can be lathe-cut, spherical shaped, or irregular shaped particles.

(5) This composition contains approximately 25-35% silver, 40-50% tin, and 23-29% copper, after blending. Each of the alloys in this composition includes the following composition (preferred amount in parenthesis):

Alloy component No. 1

Silver: 55-65% (59.3)
Tin: 25-30% (27.8)
Copper: 10-15% (12.9)

Alloy component No. 2

Tin: 55-65% (60.9)
Copper: 35-45% (39.1)

The most preferred blended composition has the following makeup:

Alloy component No. 1: 50%
Alloy component No. 2: 50%

An amalgam is made from such a blend by mixing the blend with from about 40 to about 60 percent of mercury, yielding a plastic amalgam mass suitable for use as a dental restorative material; any or all of the alloy components can be lathe-cut, spherical shaped, or irregular shaped particles.

Any of the copper-tin compounds of this invention, to be incorporated as an additive into a blend, can also be used when the blend contains other elemental additions such as indium, cadmium, aluminum, manganese, gold, silver, zinc, etc.

The following examples are set forth to further illustrate the present invention:

EXAMPLE I

A 1:1 ratio blend was prepared of (A) a commercially available spherical, high copper alloy of approximately 59.25 weight percent of silver, approximately 27.82 weight percent of tin, and approximately 12.90 weight percent of copper and (B) a lathe-cut alloy additive, $Cu_6Sn_5$, having approximately 62.0 weight percent tin and approximately 38.0 weight percent copper.

The commercial alloy (A) was prepared by weighing separately the silver, copper, and tin components to their correct proportions (mentioned above), melting these components together in an induction furnace to a molten mass, spraying the molten mass through a nozzle into an inert atmosphere such as argon or nitrogen causing it to solidify into spheres, screening the spherical particles to obtain the desired particle size distribution of from about 2 to about 60 micrometers ($\mu$m) with a mean distribution of about 25 to 30 $\mu$m, and annealing the desired particles to obtain a metallurgical crystal structure that is suitable as a dental amalgam alloy when mixed with mercury. This alloy is described in U.S. Pat. No. 3,871,876 and is herein incorporated by reference.

The additive (B) was prepared by weighing separately the copper and tin components to their correct proportions (as mentioned above), melting these components together in an induction furnace to a molten mass, pouring the molten mass into a mould and allowing it to solidify, removing the alloy ingot from the mould and annealing it to obtain the desired metallurgical crystal structure, and placing the annealed ingot on a lathe and cutting shaving therefrom. The shavings are then screened to a predetermined particle size distribution (from about 2 to about 60 $\mu$m), acid washed, and dried.

The blend of 50% of A and 50% of B was tumbled to produce a uniform admixture and placed into capsules in clinically usable quantities of 400 to 800 milligrams (mg).

A capsule and 45 percent by weight of mercury was mixed together and triturated on an S.S. White Capmaster amalgamator. The amalgam product was a plastic mass having a four minutes availability for manipulating into a prepared dental cavity. The one hour compressive strength of the amalgam was determined to be 13,700 pounds per square inch when tested according to the American Dental Association's Specification No. 1.

EXAMPLE II

An alloy blend of (i) 50% by weight of $Cu_3Sn$, (ii) 25% of a first spherical silver-tin-copper alloy, (iii) 11.875% of a second spherical silver-tin-copper alloy, and (iv) 13.125% of a lathe cut silver-tin-copper-zinc alloy was prepared. Alloy (i), $Cu_3Sn$, had 63% of copper and 37% of tin. Alloy (ii) had about 59.25% of silver, 27.82% of tin, and 12.90% of copper. Alloy (iii) had about 68.26% of silver, 26.76% of copper, and 4.39% of tin and is described in U.S. Pat. No. 3,980,472. Alloy (iv) had 71% of silver, 2.5% of copper, 25.5% of tin and 1.0% of zinc. All of the alloys of this blend were prepared by similar techniques as taught in Example I. The alloy blend was placed into a capsule; this capsule was then mixed with 48.5% mercury and triturated in a S.S. White Capmaster amalgamator. The amalgam product was a plastic mass having 3.75 minutes working time available for a dentist to manipulate the amalgam in a prepared dental cavity. The one hour compressive strength was determined to be 10,900 pounds per square inch when tested according to the American Dental Association's Specification No. 1.

What is claimed:

1. In a dental amalgamable composition comprising about 50 to 95% by weight of at least one amalgamable alloy of 40 to 75% by weight of silver, 20 to 30% by weight of tin, 2 to 30% by weight of copper, and 0.5 to 30% by weight of at least one member selected from the group consisting of indium, zinc, gold, mercury, manganese, cadmium, and aluminum, the improvement comprising adding to this composition from about 5 to about 50% by weight of at least one member selected from the group consisting of $Cu_6Sn_5$, $Cu_3Sn$, and a mixture thereof wherein the member is in the form of lathe-cut, spherical shaped, or irregular shaped particles and is composed of 30 to 70% by weight of copper and 70 to 30% by weight of tin.

2. The composition of claim 1 wherein 50% of $Cu_6Sn_5$ is added to the composition.

3. The composition of claim 1 wherein 50% of $Cu_3Sn$ is added to the composition.

* * * * *